United States Patent [19]

Meybeck et al.

[11] Patent Number: 5,198,225
[45] Date of Patent: Mar. 30, 1993

[54] HYDRATED LIPIDIC LAMELLAR PHASES OR LIPOSOMES BASED ON ECDYSTEROIDS

[75] Inventors: Alain Meybeck, Courbevoie; Frederic Bonte, Boulogne, both of France

[73] Assignee: LVMH Recherche, Colombes Cedex, France

[21] Appl. No.: 671,682

[22] PCT Filed: Oct. 2, 1989

[86] PCT No.: PCT/FR89/00507

§ 371 Date: Mar. 22, 1991

§ 102(e) Date: Mar. 22, 1991

[87] PCT Pub. No.: WO90/03778

PCT Pub. Date: Apr. 19, 1990

[30] Foreign Application Priority Data

Oct. 3, 1988 [FR] France .................................. 88 12909

[51] Int. Cl.$^5$ .............................................. A61K 9/127
[52] U.S. Cl. ..................................... 424/450; 424/401; 424/417; 428/402.2; 514/181; 514/182; 514/844

[58] Field of Search ............... 424/450, 538, 195.1, 424/401, 417; 514/181, 182, 844, 887; 428/402.2

[56] References Cited

U.S. PATENT DOCUMENTS

| | | | |
|---|---|---|---|
| 4,427,649 | 1/1984 | Dingle et al. | 424/450 |
| 4,485,054 | 11/1984 | Mezei et al. | 424/450 X |
| 4,508,703 | 4/1985 | Rodztaiak | 424/38 |
| 4,891,219 | 1/1990 | Karr, Jr. et al. | 514/12 X |

Primary Examiner—Thurman K. Oage
Assistant Examiner—G. S. Kishore
Attorney, Agent, or Firm—Bryan Cave

[57] ABSTRACT

Compositions based on hydrated lipidic lamellar phases or liposomes are disclosed containing at least in part at least one ecdysteroid or ecdysteroid derivative, in particular ecdysterone, or a plant or animal extract containing the said ecdysteroid or ecdysteroid derivative. Cosmetic or pharmaceutical compositions can be prepared as well as compositions for sericulture or a phytosanitary composition.

46 Claims, No Drawings

HYDRATED LIPIDIC LAMELLAR PHASES OR LIPOSOMES BASED ON ECDYSTEROIDS

The present invention relates essentially to compositions based on hydrated lipidic lamellar phases or liposomes containing an ecdysteroid, preferably ecdysterone, or one of its derivatives; and cosmetic, pharmaceutical, in particular dermatological, phytosanitary compositions or compositions for sericulture incorporating it.

The ecdysteroids are a group of 2,3,14-trihydroxy-$\Delta$-7-6-ketosteroids. Mention may be made of $\alpha$-ecdysone or ($2\beta,3\beta,14\alpha$-22/R/, 25-pentahydroxy-7-cholesten-6-one); 2-deoxyecdysone or ($3\beta,14\beta,22$/R/, 25-tetrahydroxy-$5\beta$-7-cholesten-6-one), ecdysterone or $\beta$-ecdysone or $2\beta,3\beta,14,20\beta,22,25$-hexahydroxy-7-cholesten-6-one; $\beta$-ecdysone-22-acetate or 20-hydroxyecdysone-22-acetate or 7-cholesten-$2\beta,3\beta,14,20,22$/R/,25-hexol-6-one-22-acetate; 5-hydroxyecdysterone or $5\beta,7$-cholesten-$2\beta,3\beta$, 5,14,20,22/R/25-heptahydroxy-6-one; $\beta$-2-deoxyecdysone or $3\beta,14,20,22$/R/25-pentahydroxy-$5\beta,7$-cholesten-6-one. The ecdysteroids, and in particular ecdysterone (in some cases called $\beta$-ecdysone or even crustecdysone) are well known in the literature and cited in the Merck Index, 10th edition, 1983, page 505, No. 3 470.

It is known that the ecdysteroids, and in particular ecdysterone, play an important role both in insects in the animal kingdom and in the plant kingdom. In insects, these hormones play a key role in growth and reproduction. Ecdysterone is implicated in particular in the various metamorphoses up to the formation of the adult insect (see CNRS publication: Biologie 1990, "Enjeux et Problématiques" by A. Berkaloff et al.).

In plants, the activity of these substances has not been completely elucidated. They seem to act on flowering (CIENCIA e Cultura (1980), volume 32, No. 10, pages 1384–1390).

Furthermore, the use of hydrated lipidic lamellar phases or liposomes in cosmetic or pharmaceutical, in particular dermatological compositions, in which various active ingredients are incorporated, is already known (FR-A-2 540 381).

It has now been discovered, in a quite surprising and unexpected manner, that the incorporation of an ecdysteroid, preferably ecdysterone, or a derivative of the said ecdysteroid, or a plant or animal extract containing the said ecdysteroid or ecdysteroid derivative, at least in part in hydrated lipidic lamellar phase or in liposomes, causes an exacerbated activity of this substance or this extract. This relates in addition, and also in a completely unexpected manner, to all known activities of the ecdysteroid previously mentioned or an extract containing the latter. An even more radical improvement of activity was observed with respect to the activity of regeneration of the cutaneous structure and of anti-aging activity.

Consequently, a synergistic effect is obtained by the incorporation of an ecdysteroid, preferably ecdysterone or an ecdysteroid derivative or a plant or animal extract containing the said ecdysteroid at least in part in hydrated lipidic lamellar phases or in liposomes.

Thus, the aim of the present invention is to resolve the novel technical problem consisting in the provision of a new formulation of ecdysteroid(s), preferably ecdysterone or a derivative of the said ecdysteroid, or a plant or animal extract containing the said ecdysteroid, making it possible to potentiate its efficacy so as to allow its use in cosmetic, pharmaceutical, in particular dermatological, compositions as well as in compositions for sericulture and phytosanitary compositions.

The present invention solves this novel technical problem satisfactorily for the first time.

Thus, in accordance with a first feature, the present invention provides a composition based on hydrated lipidic lamellar phases or liposomes, characterized in that the said hydrated lipidic lamellar phases or the said liposomes contain at least in part at least one ecdysteroid or an ecdysteroid derivative, or a plant or animal extract containing the said ecdysteroid or a derivative of the said ecdysteroid.

According to a particular embodiment, the above-mentioned ecdysteroid is ecdysterone, or a derivative of ecdysterone, in particular an acylated, hydroxylated or deoxy derivative of the latter.

According to a particularly advantageous embodiment of the invention, the derivative of ecdysterone is selected from the group consisting of $\beta$-ecdysone-2-acetate, $\beta$-ecdysone-3-acetate, $\beta$-ecdysone-2,3-diacetate, $\beta$-ecdysone-2,3,22-triacetate, $\beta$-ecdysone-2,3,22,25-tetraacetate 5-hydroxyecdysterone and 2-deoxyecdysterone.

In accordance with an alternative embodiment, the abovementioned ecdysteroid is §-ecdysone or one of its derivatives, in particular an acetate.

In accordance with another particular characteristic of the invention, the above-mentioned animal or plant extract containing the ecdysteroid, preferably ecdysterone, is an extract of *Polypodium vulgare*, *Ajuga decumbens* or *Cyanotis arachnoidea*.

In accordance with another particular characteristic of the invention, the ecdysteroid or its derivative is incorporated at least in part in the lipidic phase of hydrated lipidic lamellar phases or liposomes.

In the present description and the Claims, the term "lipidic" in the expression "lipidic phase" or "lipidic lamellar phase" covers all of the substances containing a so-called fatty carbon chain, usually of more than 5 carbon atoms.

According to the invention, amphiphilic lipids are used, i.e. those constituted of molecules possessing an ionic or non-ionic hydrophilic group and a lipophilic group, these amphiphilic lipids being capable of forming lipidic lamellar phases or liposomes in the presence of an aqueous phase. In particular, among these lipids we should mention: the phospholipids, the phosphoaminolipids, the glycolipids, the polyoxyethylene fatty alcohols, the polyol esters, optionally polyoxyethylenated. Such substances are, for example, constituted by egg white or soya lecithin, a phosphatidylserine, a sphingomyelin, a ceramide, a cerebroside or a polyglyceroloxyethylenated stearate.

In accordance with an advantageous embodiment of the invention, the concentration of the ecdysteroid is included between 0.001 and 30% by weight of the said lipidicphase and preferably between 0.01 and 10% by weight of the lipidic phase.

The preparation of the hydrated lipidic lamellar phases or liposomes containing at least in part at least one ecdysteroid according to the invention may be performed according to one of the known procedures for incorporating active substances, in particular steroids, into hydrated lipidic lamellar phases or liposomes.

The simplest procedure is that described by Bangham in J. Mol. Biol. (1965) 13, p. 238–252, which consists of dissolving the lipids in a volatile organic solvent, then of evaporating the solvent in a rotating flask so as to obtain a thin film of lipids on the inside of the rotating flask, then water is added to the rotating flask which, on shaking, gives rise to a suspension of liposomes. An improvement in this procedure consists of using ultrasonics to homogenize the liposomes obtained.

In accordance with a preferred embodiment of the present invention, a procedure for the atomization of the constituents of the lipidic phase is used, this atomization being followed by a dispersion in an aqeous medium, then optionally by homogenization under pressure, in conformity with the procedures described in U.S. Pat. No. 4,508,703 and U.S. Pat. No. 4,621,023 or U.S. Pat. No. 4,621,023.

In accordance with a preferred embodiment of the invention, the ecdysteroid or its derivative or a plant or animal extract containing it is incorporated into the lipidic phase. Thus, before atomization, the ecdysteriod or its derivative or an extract containing it, with the constituents of the lipidic phase is dissolved in an organic solution containing at least one amphiphilic lipid such as soya lecithin and, optionally, a lipophilic hydrophobic compound such as cholesterol or β-sitosterol. The solvent is preferably selected from dichloromethane, chloroform or methanol, or one of their mixtures.

The organic solution may advantageously contain an anti-oxidant such as α-tocopherol.

The lipid powder obtained is dispersed in a suitable aqueous medium, for example a PBS buffer solution, a glucose solution or a solution of sodium chloride.

In this way are obtained slightly hydrated lipidic lamellar phases or a solution of liposomes depending on whether it has been chosen to disperse the lipid powder in relatively little, i.e. from about 50% to about 90%, or much, i.e. more than 90%, of the aqueous phase as is set out in the patent previously mentioned (U.S. Pat. No. 4,508,703).

In accordance with an advantageous embodiment of the invention, particularly in the case of a liposome composition, after the composition obtained has optionally been homogenized, the compositions of hydrated lipidic lamellar phases or liposomes are gelled by being mixed with a gel such as a gel of vinyl polymer, in particular that marketed under the trade name Carbopol ® 940. This gelling procedure is also described in U.S. Pat. No. 4,508,703, in particular in the examples.

The ecdysteroids or their derivatives, preferably ecdysterone or its derivatives, are obtained in an isolated form, or in the form of an extract made from any available natural source or also made by a procedure of chemical synthesis. The main natural sources of ecdysteroids are insects and, especially, a large number of plants. A certain number of synthetic procedure has also been developed.

Extraction from Insects

The amount of ecdysteroids, in particular α or β-ecdysone, present in insects is extremely low. In the moth Bombyx mori it is, for example, $5.10^{-6}\%$ by weight of the insect (see A. Butenandt et al., Z. Naturforsch. B., 9, 389, (1954)).

The extraction of ecdysteroids from insects thus cannot usually constitute an industrial isolation procedure.

However, in the Hunger-Ricci patent CH-A-478 565, the extraction of ecdysterone from nymphs or chrysalids and destined for the preparation of cosmetic compositions, is described.

Extraction from Plants

The concentration of ecdysteroids, in particular ecdysterones, varies from one variety to another. For example, the concentration of ecdysterone is 0.025% in the seeds of *Achyranthes aspera*, 0.35% in the plant *Sesuvium portulacastrum*, and from 1.2% to 2.9% in *Cyanotis arachnoidea* depending on whether the entire plant or the roots are used. The percentages are percentages by weight of dry material.

Among the plants which may possibly be used for the extraction of the ecdysteroids, in particular ecdysterone, mention may be made of: *Serratula sogdiana* and *Rhaponticum integrifolium*, which offer the advantage that they can be cultivated (see Horticultural Abs. OCO51-01546 with reference to Rastitel'nye Resursy, (1980), volume 16, No. 2, pages 193–198 (in Russia).

Extractions from the following may also be mentioned:

*Serratula tinctoria* (HUT-029 390);
*Serratula inermis* (SU-1 146 050);
*Achyranthes fauriei*, amaranthacea, (FR-1 525 385);
Cyathula (FR-1 525 385);
*Ajuga decumbens* (JP-46-014 665);
*Pfaffia iresinoides* (Derwent 88-045806 or JP-63 002 928);
*Pfaffia paniculata* (Derwent 84-052423 or JP-59-010 600);
*Polypodium vulgare* (J. JIZBA et al. Tetrahedron Letters, (1967), page 1689, U.S. Pat. No. 3,527,777, CS 131 136);
Kaladana seed (DE-2 201 991);
*Ipomea petaloidea* (DE-2 834 703);
Silenes (HUT 029 390 and SU 924 051);
*Cyanotis arachnoidea* (C.A. 89-176352 with reference to the publication by NIEN SCHUI LIN et al. ACTA CHIMICA SINICA, 1978, volume 36, No. 2, pages 137–141 (in Chinese)).

These sources of ecdysteroids are given in a non-limiting sense and are not exhaustive.

Some extracts may also contain acetylated derivatives, in addition to ecdysterone (C.A. 89-176352).

It is also possible to obtain the ecdysteroids according to the invention by chemical synthesis (see, for example, U.S. Pat. No. 3,354,152, U.S. Pat. No. 3,354,154, U.S. Pat. No. 3,378,549, U.S. Pat. No. 3,455,905, FR-1 494 371; U.S. Pat. No. 3,440,241; FR-1 524 924; and FR-A-1 498 237).

An example of the general procedure for the extraction of ecdysteroids, preferably ecdysterone, from plants is described in Chem. Pharm. Bull. (1969) 17 (2) 340-2 by S. Imai et al.

The fresh plant is macerated in 5 times its weight of methanol, it is homogenized and filtered. This operation is repeated. The extracts are concentrated, and water is added to give a 30% methanol-water solution.

This solution is extracted with hexane. The 30% methanolic fraction is concentrated again and extracted with ethyl acetate. The aqueous fraction is extracted with n-butanol. The butanol extract is then concentrated by evaporation, and subjected to chromatography on silica gel using a chloroform-methanol mixture. After recrystallization from an ethanol-ethyl acetate mixture, ecdysterone is thus obtained in the form of colorless needles.

Furthermore, a number of ecdysteroids are commercially available. For example, ecdysterone, 5-hydroxyecdysterone, 2-deoxyecdysterone, ecdysterone 22-acetate, α-ecdysone and 2-deoxy-α-ecdysone are available from SIGMA under the catalogue numbers SIGMA H 5142, SIGMA P 9531, SIGMA D 7775, SIGMA H 5267, SIGMA E 9004, SIGMA D 7900.

The compositions according to the invention previously described, containing an ecdysteroid, preferably ecdysterone, or its derivatives in a form at least in part incorporated in hydrated lipidic lamellar phases or in liposomes find many uses.

Thus, according to a second feature of the invention, the invention relates to a cosmetic or pharmaceutical, in particular dermatological, composition characterized in that it comprises a composition based on hydrated lipidic lamellar phases or liposomes like those previously defined, containing at least in part at least one ecdysteroid or ecdysteroid derivative or a plant or animal extract containing the said ecdysteroid or ecdysteroid derivative.

Thus, the use in cosmetics and pharmacy of ecdysteroids relates in particular to anti-aging products, in particular anti-wrinkle products, after-sun regenerative products, tonic products for the hair, cicatrizing products designed to treat in particular wounds, sores, varicose ulcers or burns, anti-stretch mark products, products designed to improve the resistance of the walls of the blood vessels.

In addition, in pharmacy these substances have a hypoglycemic, lipid lowering and anti-atherosclerosis, analgesic action. Ecdysterone is also used for the preparation of anti-parasitic vaccines, in particular against bilharziosis, and to prepare anti-viral agents.

The concentration by weight of the ecdysteroid or its derivatives in the said composition is preferably included between 0.001 and 5%, and more preferably between 0.05 and 1% with respect to the total weight of the composition.

In accordance with a third feature, the present invention also relates to a composition for sericulture, characterized in that it comprises a composition according to the invention based on hydrated lipidic lamellar phases or liposomes containing at least in part at least one ecdysteroid or an ecdysteroid derivative or a plant or animal extract containing the said ecdysteroid or ecdysteroid derivative.

The concentration by weight of the ecdysteroid or its derivatives in this composition for sericulture is the standard concentration and will usually be included between 0.0001 and 1%, and preferably between 0.0005 and 0.01% with respect to the total weight of the composition.

The use of ecdysterone in sericulture is known as factor of metamorphosis in order to increase the yield of silk production by the worm of Bombyx mori (see FR-A-2 212 094, JP 46-014 665; JP 45-037 554).

Thus, the compositions according to the invention may be used by spraying onto the larvae of the silkworm or incorporated into their food.

In accordance with a fourth feature, the invention also relates to a phytosanitary composition, characterized in that it comprises a composition according to the invention based on hydrated lipidic lamellar phases or liposomes containing at least in part at least one ecdysteroid or an ecdysteroid derivative or a plant or animal extract containing the said ecdysteroid or ecdysteroid derivative The concentration used will also be the usual concentration, usually included between 0.0001 and 5% by weight, and preferably between 0.0005 and 1% by weight with respect to the total weight of the composition.

The use of the ecdysones for the production of insecticides or nematocides is known from NL-A-67 10529, JP 47-003550; DE-2 201 991; FR-A-1 498 238; CS-131 136.

In all of these uses, the incorporation at least in part of one ecdysteroid, preferably ecdysterone, in hydrated lipidic lamellar phases or in liposomes provides an unexpected increase in the activity of these substances with respect to their activity in the free state.

Thus, this constitutes quite unexpected, decisive technical progress for the person skilled in the art.

Other aims, characteristics and advantages of the invention will become apparent in the light of the explanatory description which follows made with reference to several examples of the embodiment of the invention given simply as illustrations and which thus in no way limit the scope of the invention.

Unless indicated otherwise, the percentages in the examples are given by weight.

EXAMPLE 1 ACCORDING TO THE INVENTION

Preparation of Liposomes Containing Ecdysterone 0.25 g of commercial ecdysterone, 4.5 g of soya lecithin and 0.5 g of β-sitosterol are dissolved in a dichloromethane-methanol mixture 4:1. This solution is evaporated under reduced pressure (about 200 mm of mercury) in a rotating flask warmed to 45° C. The lipid form obtained is taken up in 199.75 g of an aqueous solution containing 0.2 g/l of monopotassium phosphate and 1.44 g/l of disodium phosphate with stirring for 1 h.

A suspension of liposomes is thus obtained which is subjected to homogenization by means of ultrasonics (15 min, 150 W, 4° C.). This suspension is then gelled by mixing it with an equal weight of Carbopol ®940 gel, prepared in the standard manner at 1.25%.

250 g of a gelled composition based on liposomes are thus obtained, the ecdysterone content of which is 0.1%.

EXAMPLES 2 AND 3 ACCORDING TO THE INVENTION

Preparation of Hydrated Lipidic Lamellar Phases Containing Ecdysterone as well as Ecdysterone 22-Acetate The following compounds are dissolved in 300 ml of dichloromethane:

| | |
|---|---|
| soya lecithin | 36.0 g |
| χ-tocopherol | 0.5 g |
| β-sitosterol | 4.0 g |
| ecdysterone* | 0.3 g |
| ecdysterone-22-acetate* | 0.2 g |

*commercial

The solution obtained is sprayed according to the procedure described in the patent U.S. Pat. No. 4,508,703 at 55° C. so as to produce an intimate mixture of the constituents in the form of a fine powder. 20 g of the sprayed lipid powder thus obtained are then dispersed in 80 g of an aqueous solution such as that described in example 1 with the aid of a roller mill.

A slightly hydrated lipidic lamellar phase with about 0.24% of ecdysteroids is thus obtained (example 2).

A further 15 g of sprayed lipid powder are dispersed in 485 g of the aqueous solution previously mentioned with gentle stirring for 2 h. An aqueous suspension of very hydrated lamellar phases or liposomes is thus obtained which can be homogenized, for example, by means of a pressure homogenizer as described in the patent EP-B1-0 107 559. The homogenized suspension obtained (example 3) contains liposomes with a mean diameter of 100 nm.

The ecdysteroid content is about 0.04% by weight of the aqueous suspension.

EXAMPLE 4 ACCORDING TO THE INVENTION

Demonstration of the Activity of the Compositions According to the Invention on the Regeneration of Cutaneous Structure The activity of the compositions according to the invention on the regeneration of cutaneous structure was demonstrated in the rat by a test of the rapidity of scar formation at a cutaneous lesion.

50 hairless male rats, weighing about 250 g, are divided into 5 groups of 10 animals, one of which is the control group without treatment.

A lesion is made on each animal under Pentobarbital sodium anesthesia with the aid of a metal probe 13 mm in diameter cooled with liquid nitrogen and applied to the skin in the scapular region for 15 seconds.

The animals of 4 groups are then treated 5 days out of 7 at the site of the lesion by 0.5 ml of the product to be tested.

The groups 1 to 4 are treated respectively with the following products A to D:
  Product A: suspension of liposomes according to the invention according to example 1 with 0.1% of ecdysterone
  Product B: 0.625% Carbopol 940 ® gel containing 0.1% of free ecdysterone, comparative
  Product C: 0.625% Carbopol 940 ® gel, comparative
  Product D: suspension of liposomes prepared according to example 1, but without the incorporation of ecdysterone, comparative Every day at the time of the administration, the animals are observed to check the development of the scab formed on the lesion.

The disappearance of this scab determines the end of experimentation and the time of sacrifice of the animals, whose skin is removed for the histological study of the region treated.

The time elapsed between the beginning of treatment with the products to be tested and the disappearance of the scab is recorded in days.

The number of days of scar formation for each group is the arithmetic mean for each animal treated. Each mean is compared with the others by the Student t test. The numerical results are shown in table I.

TABLE I

| Group No. | Product | Mean (days) Standard deviation | t test | | | |
|---|---|---|---|---|---|---|
| 1 | A (invention) | 11:30 3:50 | A/B 3:35 S | A/C 2:05 (S) | A/D 5:23 (HS | A/T 3:43 S |
| 2 | B (comparative) | 23:30 10:77 | | B/C 1:55 NS | B/D 1:44 NS | B/T 0:75 NS |
| 3 | C (comparative) | 16:80 7:73 | | | C/D 3:19 S | C/T 2:07 NS |
| 4 | D (comparative) | 30:30 10:93 | | | | D/T 0:47 NS |

TABLE I-continued

| Group No. | Product | Mean (days) Standard deviation | t test |
|---|---|---|---|
| 5 | Control | 27:60 14:60 | |

These results show very clearly that the liposomes containing the ecdysterone (product A) show a significantly or very significantly higher activity than the other products tested on cutaneous regeneration after lesion. In particular, this superiority is very marked compared with the Carbopol gel containing an equal concentration of ecdysterone (product B).

Furthermore, the histological study of the scar zone gave the results shown in table II for the animals which have been treated with the products A or B.

TABLE II

Distribution of the animals according to the cicatrization reaction

| Group No. | Product | Intensity of the reaction | | | |
|---|---|---|---|---|---|
| | | +++ | ++ | + | − |
| 1 | A (invention) | 0 | 3 | 5 | 2 |
| 2 | B (comparative) | 1 | 1 | 1 | 7 |

Scoring scale:
−: strong cicatrization reaction
+: moderate cicatrization reaction
++: weak cicatrization reaction
+++: normal structures.

The cicatrization reaction is characterized by an acanthotic epidermis with a disorganised basal layer, edema at the dermo-epidermal junction, the presence of many fibroblasts in the dermis.

Thus, the better the restructuring of the skin after lesion, the weaker the cicatrization reaction.

Here again it seems clear that the product A (composition according to the invention) exhibits a better restructuring activity than product B (free ecdysterone).

EXAMPLE 5

Dermatological Gel According to the Invention

The composition according to example 1 may be used as such as a dermatological composition in the form of a gel.

This gel is used particularly in cases of burns, chapped skin or wounds, for a period of about 8 to 15 days and preferably twice a day.

It is particularly useful for speeding up the cicatrization of surgical wounds and in particular in plastic surgery.

EXAMPLE 6

After-Sun Cosmetic Composition According to the Invention

After being mixed 50—50 (by weight) with a 2% Carbopol 940 ® gel, the gel composition according to example 3 may be used as a restorative cosmetic composition for solar elastosis and actinic aging.

In this case, this composition is preferably applied twice a day for three weeks to the areas to be treated.

EXAMPLE 7

Cosmetic Cream According to the Invention to Combat the Effects of Aging

The composition of the cream is the following:

| | |
|---|---|
| soya lecithin | 1.95 g |
| β-sitosterol | 0.05 g |
| ecdysteroids | 0.2 g |
| (made up of: | |
| ecdysterone* | 0.12 g |
| ecdysterone-22-acetate* | 0.08 g |
| excipients for the emulsion | |
| oil in water, + preservatives + perfumes | qsp 100 g |

*commercial

A suspension of liposomes according to example 3, on the one hand, and an oil-in-water emulsion based on squalane, on the other, are prepared separately.

These two preparations are then mixed, for example by means of a helical stirrer at moderate speed in a ratio of 1 volume of liposome suspension to 5 volumes of emulsion.

The cream obtained applied daily to the face allows the skin to regain and maintain its youthful and sparkling appearance.

We claim:

1. A composition comprising hydrated lipidic lamellar phases or liposomes containing at least one ecdysteroid in a concentration ranging between 0.0001 and 5% by weight of the composition.

2. The composition of claim 1, wherein the ecdysteroid is selected from the group consisting of ecdysterone, an acylated ecdysterone, an hydroxylated ecdysterone, a deoxyecdysterone, α-ecdysone, 2-deoxyecdysone and a β-ecdysone acetate.

3. The composition of claim 1, wherein the ecdysteroid is selected from the group consisting of ecdysterone, β-ecdysone-2-acetate, β-ecdysone-3-acetate, β-ecdysone-2,3-diacetate, β-ecdysone-2,3,22-triacetate, β-ecdysone-2,3,22,25-tetraacetate, 5-hydroxyecdysterone, and 2-deoxyecdysterone.

4. The composition of claim 1, wherein the ecdysteroid is ecdysterone.

5. The composition of claim 1, wherein the ecdysteroid is extracted from a plant selected from the group consisting of *Polypodium vulgare, Ajuga decumbens*, and *Cyanotis arachnoidea*.

6. The composition of claim 1, wherein the ecdysteroid is at least partially incorporated into the lipidic phase of the hydrated lipidic lamellar phases or liposomes.

7. The composition of claim 6, wherein the concentration of the ecdysteroid ranges between 0.001 and 30% by weight of said lipidic phase.

8. The composition of claim 1, wherein the concentration of the ecdysteroid ranges between 0.001 and 5% by weight of the composition.

9. The composition of claim 6, wherein the concentration of the ecdysteroid ranges between 0.01 and 10% by weight of said lipidic phase.

10. A cosmetic or pharmaceutical composition comprising hydrated lipidic lamellar phases or liposomes containing at least one ecdysteroid in a concentration ranging between 0.001 and 5% by weight of the composition, in admixture with a cosmetically or pharmaceutically acceptable excipient.

11. The composition of claim 10, wherein the concentration of the ecdysteroid ranges between 0.05 and 1% by weight of the composition.

12. The composition of claim 10, wherein the ecdysteroid is selected from the group consisting of ecdysterone, an acylated ecdysterone, an hydroxylated ecdysterone, a deoxyecdysterone, β-ecdysone, 2-deoxyecdysone and a β-ecdysone acetate.

13. The composition of claim 10, wherein the ecdysteroid is selected from the group consisting of ecdysterone, β-ecdysone-2-acetate, β-ecdysone-3-acetate, β-ecdysone-2,3-diacetate, β-ecdysone-2,3,22-triacetate, β-ecdysone-2,3,22,25-tetraacetate, 5-hydroxyecdysterone, and 2-deoxyecdysterone.

14. The composition of claim 10, wherein the ecdysteroid is ecdysterone.

15. The composition of claim 10, wherein the ecdysteroid is extracted from a plant selected from the group consisting of *Polypodium vulgare, Ajuga decumbens*, and *Cyanotis arachnoidea*.

16. The composition of claim 10, wherein the ecdysteroid is at least partially incorporated into the lipidic phase of the hydrated lipidic lamellar phases or liposomes.

17. The composition of claim 16, wherein the concentration of the ecdysteroid ranges between 0.001 and 30% by weight of said lipidic phase.

18. The composition of claim 16, wherein the concentration of the ecdysteroid ranges between 0.01 and 10% by weight of said lipidic phase.

19. A composition for sericulture comprising hydrated lipidic lamellar phases or liposomes containing at least one ecdysteroid in a concentration ranging between 0.0001 and 1% by weight of the composition.

20. The composition of claim 19, wherein the concentration of the ecdysteroid ranges between 0.0005 and 0.01% by weight of the composition.

21. The composition of claim 19, wherein the ecdysteroid is selected from the group consisting of ecdysterone, an acylated ecdysterone, an hydroxylated ecdysterone, a deoxyecdysterone, α-ecdysone, 2-deoxyecdysone and a β-ecdysone acetate.

22. The composition of claim 19, wherein the ecdysteroid is selected from the group consisting of ecdysterone, β-ecdysone-2-acetate, β-ecdysone-3-acetate, β-ecdysone-2,3-diacetate, β-ecdysone-2,3,22-triacetate, β-ecdysone-2,3,22,25-tetraacetate, 5-hydroxyecdysterone, and 2-deoxyecdysterone.

23. The composition of claim 19, wherein the ecdysteroid is ecdysterone.

24. The composition of claim 19, wherein the ecdysteroid is extracted from a plant selected from the group consisting of *Polypodium vulgare, Ajuga decumbens*, and *Cyanotis arachnoidea*.

25. The composition of claim 19, wherein the ecdysteroid is at least partially incorporated into the lipidic phase of the hydrated lipidic lamellar phases or liposomes.

26. The composition of claim 25, wherein the concentration of the ecdysteroid ranges between 0.001 and 30% by weight of said lipidic phase.

27. The composition of claim 25, wherein the concentration of the ecdysteroid ranges between 0.01 and 10% by weight of said lipidic phase.

28. A phytosanitary composition comprising hydrated lipidic lamellar phases or liposomes containing at least one ecdysteroid in a concentration ranging between 0.0001 and 5% by weight of the composition.

29. The composition of claim 28, wherein the concentration of the ecdysteroid ranges between 0.0005 and 1% by weight of the composition.

30. The composition of claim 28, wherein the ecdysteroid is selected from the group consisting of ecdysterone, an acylated ecdysterone, an hydroxylated ecdysterone, a deoxyecdysterone, α-ecdysone, 2-deoxyecdysone and a β-ecdysone acetate.

31. The composition of claim 28, wherein the ecdysteroid is selected from the group consisting of ecdysterone, β-ecdysone-2-acetate, β-ecdysone-3-acetate, β-ecdysone-2,3-diacetate, β-ecdysone-2,3,22-triacetate, β-ecdysone-2,3,22,25-tetraacetate, 5-hydroxyecdysterone, and 2-deoxyecdysterone.

32. The composition of claim 28, wherein the ecdysteroid is ecdysterone.

33. The composition of claim 28, wherein the ecdysteroid is extracted from a plant selected from the group consisting of *Polypodium vulgare, Ajuga decumbens*, and *Cyanotis arachnoidea*.

34. The composition of claim 28, wherein the ecdysteroid is at least partially incorporated into the lipidic phase of the hydrated lipidic lamellar phases or liposomes.

35. The composition of claim 34, wherein the concentration of the ecdysteroid ranges between 0.001 and 30% by weight of said lipidic phase.

36. The composition of claim 34, wherein the concentration of the ecdysteroid ranges between 0.01 and 10% by weight of said lipidic phase.

37. A method for regenerating the cutaneous structure, comprising applying to the area of the skin to be treated, in an amount sufficient to regenerate the cutaneous structure, a composition comprising hydrated lipidic lamellar phases or liposomes containing at least one ecdysteroid in a concentration ranging between 0.001 and 5% by weight of the composition.

38. The method of claim 37, for producing an anti-wrinkling effect on the skin.

39. The method of claim 37, for producing a cicatrizing effect on the skin.

40. The method of claim 37, for producing an anti-aging effect on the skin.

41. The method of claim 37, for producing a tonic effect on the hair.

42. The method of claim 37, wherein the ecdysteroid is selected from the group consisting of ecdysterone, an acylated ecdysterone, an hydroxylated ecdysterone, a deoxyecdysterone, α-ecdysone, 2-deoxyecdysone and a β-ecdysone acetate.

43. The method of claim 37, wherein the ecdysteroid is selected from the group consisting of ecdysterone, β-ecdysone-2-acetate, β-ecydysone-3acetate, β-ecdysone-2,3-diacetate, β-ecdysone-2,3,22-triacetate, β-ecdysone-2,3,22,25-tetraacetate, 5-hydroxyecdysterone, and 2-deoxyecdysterone.

44. The method of claim 37, wherein the ecdysteroid is at least partially incorporated into the lipidic phase of the hydrated lipidic lamellar phases or liposomes.

45. The method of claim 44, wherein the concentration of the ecdysteroid in the lipidic phase ranges between 0.001 and 30% by weight of said lipidic phase.

46. The method of claim 44, wherein the concentration of the ecdysteroid in the lipidic phase ranges between 0.01 and 10% by weight of said lipidic phase.

* * * * *